United States Patent [19]

Nishizono

[11] Patent Number: 4,872,463
[45] Date of Patent: Oct. 10, 1989

[54] CONDOM APPLICATOR

[75] Inventor: Taiji Nishizono, Kuki, Japan
[73] Assignee: K.K. Chibakou Shoji, Chiba, Japan
[21] Appl. No.: 72,332
[22] Filed: Jul. 13, 1987
[30] Foreign Application Priority Data Sep. 12, 1986 [JP] Japan .................................. 61-141212

[51] Int. Cl.<sup>4</sup> ................................................ A61F 5/44
[52] U.S. Cl. ..................................... 128/844; 604/349
[58] Field of Search ............... 128/132 R, 138 R, 830, 128/842, 844; 604/349, 350, 351, 352, 353, 317, 346, 347

[56] References Cited

FOREIGN PATENT DOCUMENTS

| 0111720 | 12/1928 | Austria ................................... 604/349 |
| 1026044 | 3/1958 | Fed. Rep. of Germany ... 128/132 R |
| 241097 | 12/1974 | Fed. Rep. of Germany ....... 604/349 |
| 0211448 | 11/1984 | Japan .................................... 604/349 |
| 0070665 | 3/1942 | Switzerland .......................... 604/349 |

Primary Examiner—C. Fred Rosenbaum
Assistant Examiner—Mario Costantino
Attorney, Agent, or Firm—Ladas & Parry

[57] ABSTRACT

The primary objective of the invention is to facilitate the application of a condom without entraining air into it, by making use of the arrangements and instrumentalities shown in the accompanying drawing as a preferred embodiment of the present invention and not as limitative thereto. In the preferred embodiment, the pocket at the tip of the condom from which air is forced out as by twisting is held in a slit cut in the center of a rectangular strip applied on the condom from one side of its base along the length to the tip and then back along to the other side of the base, and which is provided with pull tabs extended laterally from the center of said strip where the slit is out.

Both ends of the strip are rolled in together with the base hem ring of the condom to form a tucked-up disk. To apply the condom to the penis, it is only required to pull the pull tabs backward along the penis to unroll the condom sheath over it while keeping the center of said tucked-up disk in close contact with the glans. In this way, the condom can be applied quickly without extraining air into it.

3 Claims, 2 Drawing Sheets

CONDOM APPLICATOR

BACKGROUND OF THE INVENTION

1. Industrial Application

The present invention relates to a condom applicator that enables the condom user to put on the condom quickly while preventing the entrainment of air into the pocket at the tip of the condom.

2. Conventional Art

While there have been such condom applicators that have a string or stip enrolled along the lengthwise direction of the condom sheath to permit the user to unroll the condom sheath upon his penis easily by pulling such string or strip, they all suffer from primarily the same problem. All of the prior devices known to Applicant are difficult or at least inconvenient to perate particularly when putting on the condom while arresting the entrainment of air into the pocket at its tip. For instance, the user is required to give two or three twists to the pocket, apply the twisted part to the head of the penis, and unroll the condom over the penis while carefully stroking the condom sheath as it runs backward to squeeze air out through between the penis and the hem ring.

A BRIEF DESCRIPTION OF THE DRAW

DETAILED DESCRIPTION OF THE INVENTION

Figure 1:
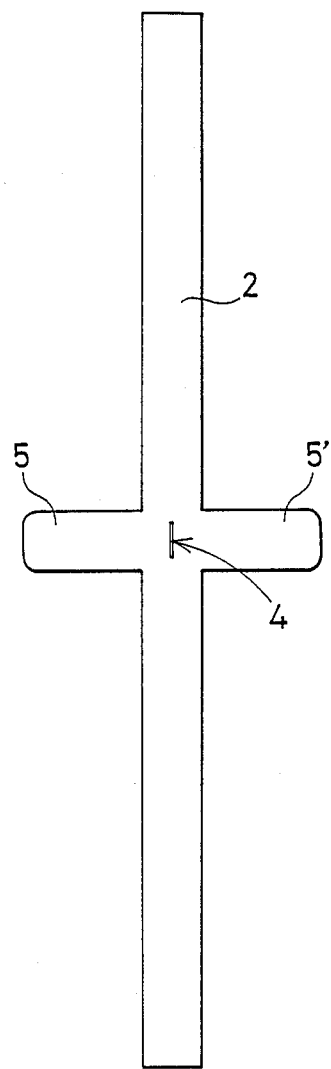
FIG. 1 is a development of a preferred embodiment of the present invention.

Referring to the drawing attached hereto, there is shown one preferred embodiment of the present invention to achieve the objective stated above; it consists of a rectangular strip (2) which is tucked in together with the hem ring (1) of the condom, and a slit (4) out into the center of said strip (2) to hold the pocket (3) at the tip of the condom, and pull tabs (5) and (5') extended on both sides of said slit (4).

ADVANTAGES OF THE INVENTION

In the preferred embodiment of the invention referred to above, the pocket (3) at the tip of the condom from which air is forced out as by twisting is held in a slit (4) cut in the center of a rectangular strip (2) applied on the condom from one side of its base hem ring (1) along the length to the tip and then back along to the other side of the base hem ring (1), and which is provided with pull tabs (5) and (5') extended laterally from the center of said strip (2) where the slit (4) is cut.

Both ends of the strip (2) are rolled in together with the base hem ring (1) of the condom to form a tucked-up disk. To apply the condom to the penis, it is only required to pull the pull tabs (5) and (5') backward along the penis to remove said strip (2) and thus to unroll the condom sheath over the penis while keeping the center of said tucked-up disk in close contact with the glans. By pulling the pull tabs (5) and (5'), the pocket (3) slips off the slit (4), and the condom sheath is unfolded over the penis quickly as the strip (2) comes off the condom.

If the pocket (3) which is emptied of air in advance as by twisting it is held in the slit (4) in the center of the strip (2), the slit (4) closes the pocket at its neck and does not allow air into the pocket (3) before application of the condom. The application of the condom to the penis is carried out simply; first, keep the inside center of the tucked-up disk into which the condom along with the strip (2) is formed in close contact with the glans with the pocket (3) closed by the slot (4), and pull the pull tabs (5) and (5') backward along the penis to unfold the condom sheath over the penis while removing the strip (2). In this way, the condom can be fitted closely in position without entraining air into the pocket (3).

PREFERRED EMBODIMENT

For the purpose of illustrating the invention, there is shown in the accompanying drawing one form which is presently preferred; it being understood that the invention is not intended to be built to the precise arrangements and instrumentalities shown.

FIG. 1 is a development of a condom applicator according to the present invention; it consists of a strip (2) made of plastic film or some other proper material with proper resilience and having a slit (4) at its center which is cut in the lengthwise direction of the strip (2) to hold the pocket (3) at the tip of the condom, and also having short pull tabs (5) and (5') flanged out of the center of the strip (2).

Figure 2:
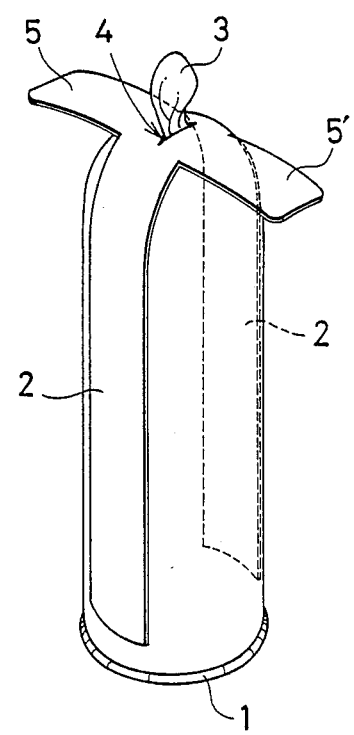
FIG. 2 is an oblique projection illustrating the pocket at the condom tip being held in the slit cut in the center of the condom applicator.

FIG. 2 is an overall view showing the combination of the condom applicator shown in FIG. 1 and a condom in which the pocket (3) at the tip of the condom from which air is forced out as by twisting is held in the slit (4) in the center of the rectangular strip (2) made of a plastic film or the like, thereby closing the pocket (3) at its neck.

Figure 3:
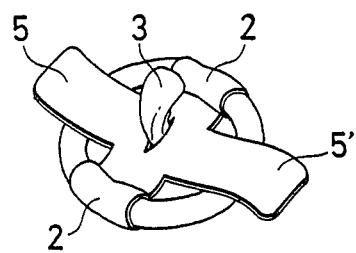
FIG. 3 is a tucked-up disk into which the assembly of the condom applicator and condom shown in FIG. 2 is rolled.

FIG. 3 is a tucked-up disk into which the combination illustrated in FIG. 2 is formed by rolling the strip (2) and condom outward together from the bottom up.

Figure 4:
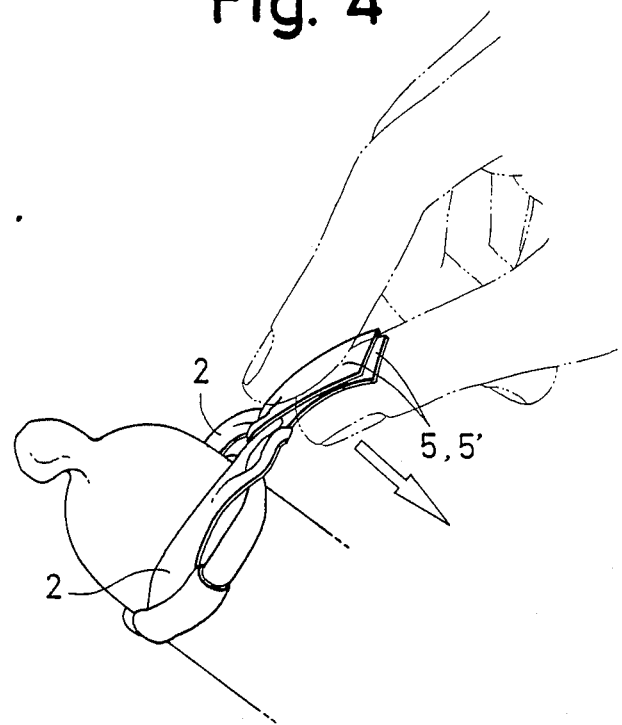
FIG. 4 is an illustration showing how to use the condom applicator according to the present invention.

FIG. 4 illustrates a method of using the condom applicator. Namely, the inside back of the condom is applied to the glans first, and the pull tabs (5) and (5') are pulled backward along the penis to remove the interleaved strip (2) to unroll the condom sheath upon the penis.

EFFECTS OF THE INVENTION

The condom applicator according to the present invention makes it possible for the user to put on a condom upon his penis quickly and conveniently without fail while arresting the air stealing into the pocket (3) at the tip of the condom.

It can be made of plastic film or the like in a simple blanking process, and can be fitted to a condom by holding into its slit (4) of the strip (2) the pocket (3) at the condom tip which is emptied of air in advance as by twisting and then by unrolling the condom and the strip (2) together from the bottom hem ring up into a tucked-up disk ready for use. The process is so simple that the condom applicator/condom combination lends itself to mass production for the benefit of both the manufacturer and user.

What is claimed is:

1. A condom applicator for use with a condom having a hem ring at one end, a sheath, and a pocket at the end remote from the hem ring, the condom applicator comprising a single and continuous strip for being placed on opposing sides of the sheath and to be rolled therewith, the strip in use extending over the pocket and including a slot through which the pocket is adapted to pass, and at least one pull tab attached to the strip along the length thereof near the slot, wherein pulling upon the tab causes the condom to unroll.

2. A condom applicator as claimed in claim 1 having a pair of tabs on each side of the strip and extending perpendicular thereto.

3. A condom applicator for use with a condom having a hem ring at one end, a sheath, and a pocket at the end remote from the hem ring, the condom applicator comprising a single and continuous strip for being placed on opposing sides of the sheath and to be rolled therewith, the strip in use extending over the pocket and including a slot through which the pocket is adapted to pass, and be held in a substantially airtight manner, and at least one pull tab attached to the strip along the length thereof near the slot, wherein pulling upon the tab causes the condom to unroll.

* * * * *